United States Patent [19]
Koko et al.

[11] Patent Number: 5,948,775
[45] Date of Patent: Sep. 7, 1999

[54] 2- OR 3-(SUBSTITUTEDAMINOALKOXYPHENYL)QUINAZOLIN-4-ONES

[75] Inventors: Marci Catherine Koko, Wayne; Arthur Attilio Santilli, Havertown, both of Pa.

[73] Assignee: American Home Products Corporation, Madison, N.J.

[21] Appl. No.: 09/041,184

[22] Filed: Mar. 12, 1998

Related U.S. Application Data

[60] Provisional application No. 60/041,088, Mar. 19, 1997.
[51] Int. Cl.$^6$ .................. A61K 31/505; C07D 239/91
[52] U.S. Cl. .................. 514/212; 514/259; 514/234.8; 544/116; 544/289; 540/600
[58] Field of Search .................. 514/259, 212, 514/234.8; 544/289, 116; 540/600

[56] References Cited

U.S. PATENT DOCUMENTS

| | | | |
|---|---|---|---|
| 3,231,572 | 1/1966 | Hayao | 260/256.4 |
| 3,265,697 | 8/1966 | Schipper | 260/256.4 |
| 4,908,448 | 3/1990 | Aldag et al. | 544/289 |

FOREIGN PATENT DOCUMENTS 9708153   3/1997   WIPO .

*Primary Examiner*—Richard L. Raymond
*Assistant Examiner*—Ann Razgunas
*Attorney, Agent, or Firm*—Robert F. Boswell, Jr.; Steven R. Eck

[57] ABSTRACT

This invention relates to 2- or 3-(substituted aminoalkoxyphenyl)quinazolin-4-ones which are partial estrogen agonists and are useful in treating osteoporosis, prostatic hypertrophy, breast cancer and endometrial cancer.

11 Claims, No Drawings

2- OR 3-(SUBSTITUTEDAMINOALKOXYPHENYL) QUINAZOLIN-4-ONES

This application claims benefit of priority to U.S. provisional patent application Ser. No. 60/041,088 filed Mar. 19, 1997.

FIELD OF INVENTION

This invention relates to 2- or 3-(substitutedaminoalkoxyphenyl)quinazolin-4-ones which are partial estrogen agonists and have potential use in treating osteoporosis, prostatic hypertrophy, breast cancer and endometrial cancer.

BACKGROUND OF THE INVENTION

Estrogen replacement therapy has been well established as the treatment of choice in women for the prevention of osteoporosis. [C. Christiansen, R. Lindsay, *Estrogen, Bone Loss and Preservation,* Osteoporosis International, 1, 15–21 (1990)] The downside to this therapy is that when estrogen is given alone i.e. without the opposing effects of progestins, proliferative effects on the uterus may result and thereby can put the patient at risk for endometriosis and/or endometrial cancer. Although less clear, unopposed estrogen replacement therapy has been implicated in increasing the incidence of breast tumor formation. Non-steroidal antiestrogen drugs such as Tamoxifen have been used in the treatment of breast cancer. The drug also is known to increase bone mass, acting as a bone-sparing estrogen agonist in bone while acting as an antagonist in uterine tissue. The drug, however, has been demonstrated to have partial agonist effects in the uterus, which therefore is of some concern. A more recent antiestrogen drug, Lilly's Raloxifene, is a non-steroidal antiestrogen which appears to be more tissue selective. While having the desirable property of sparing bone, it has been demonstrated to stimulate uterine growth in animal models to a lesser degree than Tamoxifen. A review on the tissue selective action of estrogen analogs has recently appeared. [G. L. Evans and R. T. Turner, *Tissue Selective Actions of Estrogen Analogs,* Bone, 17, no. 4, 181S–190S (1995)]

The compounds described in the present invention are partial estrogen agonists and have potential use in treating osteoporosis, prostatic hypertrophy, breast cancer and endometrial cancer.

SUMMARY OF THE INVENTION

The compounds of this invention are represented by the formula

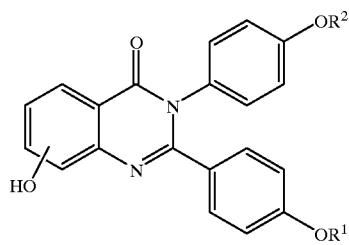

wherein:

$R^1$ and $R^2$ are H or —$(CH_2)_n$—$NR^3R^3$ where n is 2–3 and $NR^3R^4$ is pyrrolidinyl, piperidinyl, homopiperidinyl, or morpholinyl;

with a proviso that one but not both of $R^1$ and $R^2$ is hydrogen;

and the pharmaceutically acceptable salts thereof.

Pharmaceutically acceptable salts are those formed with an invention compound having a basic nitrogen and a pharmaceutically acceptable acid, including but not limited to the inorganic and organic acids such as hydrochloric, hydrobromic, hydroiodic, nitric, sulfuric, phosphoric, acetic, succinic, fumaric, maleic, malic, methanesulfonyl, benzoic, tartaric and lactic acids.

DETAILED DESCRIPTION OF THE INVENTION

The invention compounds where $R^1$ is H or $R^2$ is H are prepared from 3- or 4-methoxyisatoic anhydrides according to Schemes I and II respectively.

Scheme I
$R^1$ is H

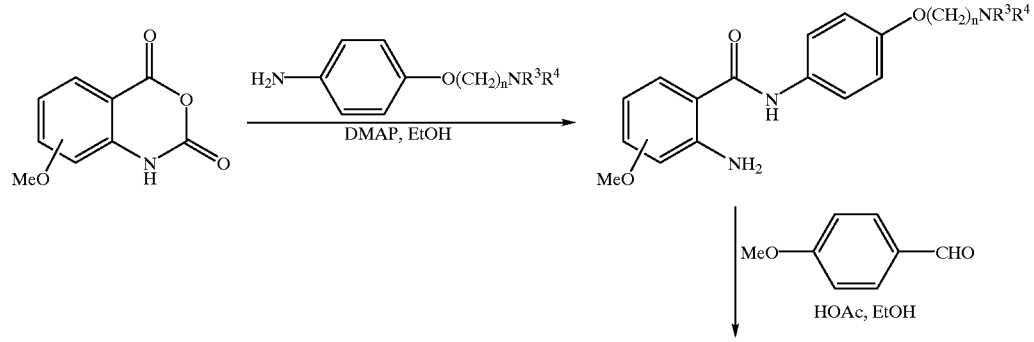

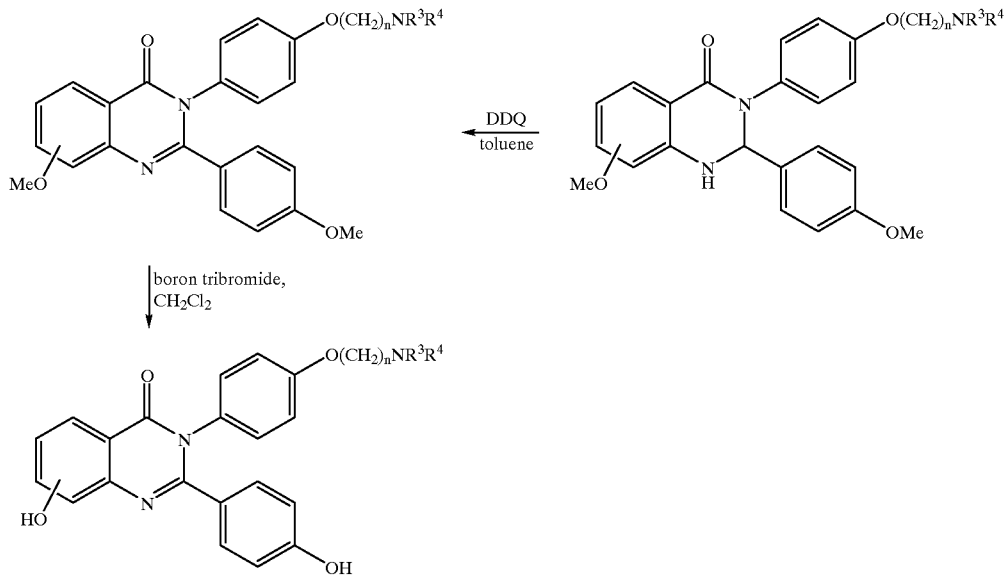
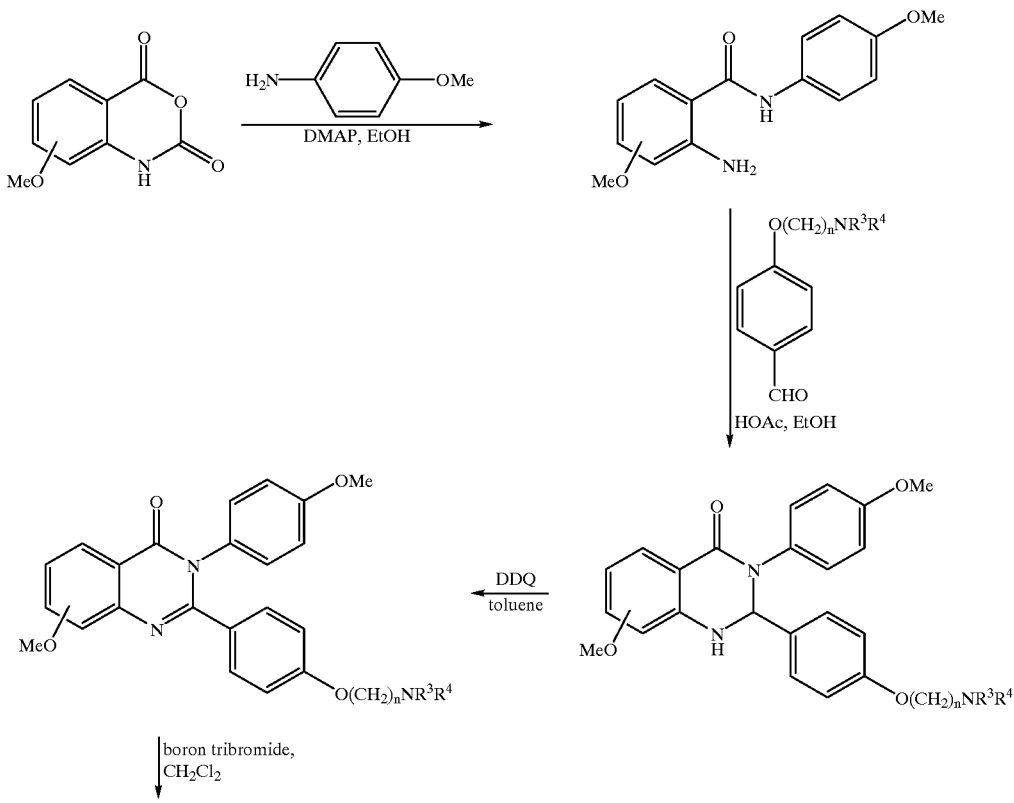
Scheme II
R² is H

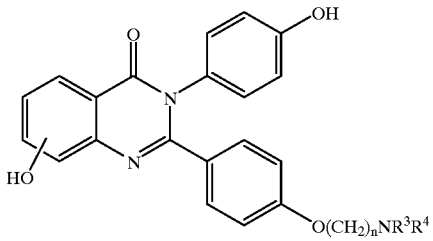

The intermediate 7- or 8-methoxyisatoic anhydrides (Examples 4 and 11 respectively) are prepared by reacting 3- (or 4)-methoxy-anthranilic acid with triphosgene (bis(trichloromethyl)carbonate) in methylene chloride. 4-Methoxyanthranilic acid is prepared according to the procedures given in examples 1–3. 3-Methoxyanthranilic acid is commercially available.

The following specific examples are included for illustrative purposes only and are not to be considered as limiting to this disclosure. The reagents and intermediate used in the following examples are either commercially available or can be prepared according to standard literature procedures by those skilled in the art of organic synthesis.

EXAMPLE 1

4-Cyano-3-nitroanisole

To a solution of 50.0 g (0.261 mol) of 4-bromo-3-nitroanisole (Lancaster Chemicals) in 150 mL of dry N,N-dimethylformamide was added 38.6 g (0.431 mol) of copper (I) cyanide, 0.73 g (0.00325 mol) of palladium(II) acetate, and 3.2 g (0.0193 mol) of potassium iodide, under nitrogen. The reaction mixture was stirred and heated under reflux for 2 hours. After cooling to room temperature, 300 mL of ethyl acetate was added to the reaction mixture. The ethyl acetate was decanted, leaving behind a dark residue on the bottom of the reaction flask. The ethyl acetate solution was extracted with saturated brine (3×150 mL), dried over magnesium sulfate, filtered and evaporated to dryness in a rotary evaporator to yield 24.5 g of orange crystals. An analytical sample (mp 136–138° C.) was obtained by recrystallization from ethyl acetate.

Elemental analysis for $C_8H_6N_2O_3$: Calc'd: C, 53.94; H, 3.39; N, 15.73; Found: C, 53.98; H, 3.21; N, 15.67.

EXAMPLE 2

2-Amino-4-methoxybenzamide

To a solution of 37.4 g (0.210 mol) of 4-cyano-3-nitroanisole in 500 mL of ethanol was added 221.6 g (0.982 mol) of tin(II) chloride dihydrate. The reaction mixture was stirred and heated under reflux for 1 hour. After cooling to room temperature, the reaction mixture was poured onto ice. Aqueous sodium bicarbonate was added slowly to the ice mixture until the solution reached pH 7–8. Additional water was added to the mixture, which was then extracted with methylene chloride (2×400 mL) and ethyl acetate (1×300 mL). The separated aqueous layers were filtered between each of the extractions. The off white residue collected on the filters was rinsed with methylene chloride and ethyl acetate several times. The combined organic phases were then dried over magnesium sulfate, filtered and evaporated in the rotary evaporator to obtain 28.5 g crude product (mp 154–155° C.).

Elemental analysis for $C_8H_{10}N_2O_2$: Calc'd: C, 57.82; H, 6.07; N, 16.86; Found: C, 57.95; H, 5.95; N, 16.78.

EXAMPLE 3

2-Amino-4-methoxybenzoic acid

A solution of 27.4 g (0.165 mol) of 2-amino-4-methoxybenzamide in 500 mL of 1N sodium hydroxide was stirred and heated under reflux for 18 hours. After the reaction mixture had cooled to room temperature the solution was brought to pH 6–7 with 0.5N HCl. A white precipitate formed which was collected by vacuum filtration. The crystals were rinsed with water and dried overnight at 100° C. The product amounted to 23.9 g. An analytical sample (mp 176–178° C.) was obtained by recrystallization from ethyl acetate.

Elemental analysis for $C_8H_9NO_3$: Calc'd: C, 57.48; H, 5.43; N, 8.38; Found: C, 57.21; H, 5.38; N, 8.34.

EXAMPLE 4

7-Methoxyisatoic anhydride

To a chilled (0–5° C.) solution of 22.9 g (0.137 mol) of 2-amino-4-methoxybenzoic acid in 500 mL of tetrahydrofuran was added 13.6 g (0.0457 mol) of triphosgene. A precipitate formed after the addition of the triphosgene. The ice bath was removed after 15 minutes, and the reaction mixture was stirred for 1 hour at room temperature. The reaction mixture was poured into 1000 mL of water and stirred for thirty minutes. The product was filtered and amounted to 22.4 g. An analytical sample (mp 215–217° C.) was obtained by recrystallization from ethyl acetate.

Elemental analysis for $C_9H_7NO_4$: Calc'd: C, 55.96; H, 3.65; N, 7.25; Found: C, 55.71; H, 3.39; N, 7.25.

EXAMPLE 5

2-Amino-N-[4-(2-chloro-ethoxy)-phenyl]-4-methoxy-benzamide

To a solution of 11.11 g (0.0575 mol) of 7-methoxyisatoic anhydride in 300 mL of ethanol was added a catalytic amount of 4-dimethylaminopyridine and 144 mL of a 1M solution containing 24.7 g (0.144 mol) of 4-(2-chloroethoxy)-aniline. The reaction mixture was sired and heated under reflux for 3 hours. One half of the solvent was evaporated in a rotary evaporator. The reaction mixture was then cooled on ice. The precipitate that formed was collected by vacuum filtration and amounted to 16.4 g. An analytical sample (mp 167–168° C.) was obtained by recrystallization from ethanol.

Elemental analysis for $C_{16}H_{17}ClN_2O_3$: Calc'd: C, 59.91; H, 5.34; N, 8.73; Found: C, 59.92; H, 5.27; N, 8.50.

EXAMPLE 6

3-[4-(2-Chloro-ethoxy)-phenyl]-7-methoxy-2-(4-methoxy-phenyl)-2,3,-dihydro-1H-quinazolin-4-one To a solution of 14.9 g (0.0465 mol) of 2-amino-N-[4-(2-chloro-ethoxy)-phenyl]-4-methoxy-benzamide in 300 mL of ethanol was added 5.6 mL (0.0465 mol) of p-anisaldehyde and 30 mL of acetic acid. The reaction mixture was stirred and heated under a mild reflux overnight. After cooling to room temperature, the solvent was evaporated in a rotary evaporator. After the addition of diethyl ether and petroleum ether, the oily residue was chilled on ice. The precipitate that formed was collected by vacuum filtration. An analytical sample (mp 157–158° C. was obtained by recrystallization from ethanol.

Elemental analysis for $C_{24}H_{23}ClN_2O_4$: Calc'd: C, 65.83; H, 5.06; N, 6.40; Found: C, 65.57; H, 5.25; N, 6.19.

EXAMPLE 7

3-[4-(2-Chloro-ethoxy)-phenyl]-7-methoxy-2-(4-methoxy-phenyl)-3H-quinazolin-4-one To a solution of 8.1 g (0.0185 mol) of 3-[4-(2-chloro-ethoxy)-phenyl]-7-methoxy-2-(4methoxy-phenyl)-2,3-dihydro-1H-quinazolin-4-one in 300 mL of toluene was added 4.2 g (0.0185 mol) of 2,3-dichloro-5,6-dicyano-1,4-benzoquinone. The reaction mixture was stirred and heated to reflux for 2 hours. The toluene was removed in a rotary evaporator. Ethanol (300 mL) was added to the reaction flask which was allowed to stir at room temperature overnight. The precipitate was collected by vacuum filtration and amounted to 6.9 g. The product (mp 186–187° C.) was used in the next step without further purification.

EXAMPLE 8

3-[4-(2-Chloro-ethoxy)-phenyl]-7-hydroxy-2-(4-hydroxy-phenyl)-3H-quinazolin-4-one To a chilled (−30° C.) solution of 1.0 g (0.00229 mol) of 3-[4-(2-chloro-ethoxy)-phenyl]-7-methoxy-2-(4-methoxy-phenyl)-3H-quinazolin-4-one in 300 mL of dry methylene chloride was added 23 mL (0.0229 mol) of boron tribromide (1M solution in dichloromethane (Aldrich Chemicals)). The reaction mixture was stirred at −30° C. for 20 minutes, under nitrogen, and then at room temperature overnight. The crude reaction mixture was added to 700 mL of aqueous sodium bicarbonate. The solution was stirred vigorously for 40 minutes at room temperature. The precipitate which formed was collected by vacuum filtration. The crude product when subjected to HPLC gave pure product. (mp 285–287° C.)

Elemental analysis for $C_{22}H_{17}ClN_2O_4$: Calc'd: C, 64.63; H, 4.19; N, 6.85; Found: C, 64.35; H, 4.08; N, 6.78.

EXAMPLE 9

7-Hydroxy-2-(4-hydroxy-phenyl)-3-{4-[2-(piperidin-1-yl)-ethoxy]-phenyl}-3H-quinazolin-4-one A solution containing 0.25 g (0.000612 mol) of 3-[4-(2-chloro-ethoxy)-phenyl]-7-hydroxy-2-(4-hydroxy-phenyl)-3H-quinazolin-4-one in 7 mL of piperidine was stirred and heated to reflux for 2 hours. After cooling to room temperature, ethyl acetate was added to the reaction mixture and the solvents were co-evaporated to near dryness in a rotary evaporator. The dark residue was extracted with ethyl acetate and water. The aqueous layer was removed and chilled on ice. The precipitate which then formed was collected by vacuum filtration (0.052 g, mp 185–190° C.) and was shown to be the hydrochloride salt monohydrate.

Elemental analysis for $C_{27}H_{27}N_3O_4.HCl.H_2O$: Calc'd: C, 63.34; H, 5.91; N, 8.21; Found: C, 63.17; H, 5.63; N, 8.14.

EXAMPLE 10

4-(2-Chloroethoxy)-aniline

To a solution of 50.27 g (0.333 mol) of 4-acetamidophenol (Aldrich Chemicals) in 700 mL of acetone was added 24.0 g (0.428 mol) of potassium hydroxide and 78.0 g (0.333 mol) of 2-chloroethyl-p-toluene sulfonate (Aldrich Chemicals). The reaction mixture was stirred and heated under reflux overnight. The solvent then was removed in a rotary evaporator. The crude crystals were collected and dissolved in 400 mL of ethyl acetate and then washed with water (3×200 mL). The organic phase was removed, dried over magnesium sulfate, filtered and evaporated in a rotary evaporator to yield 45.3 g of 4-(2-chloro-ethoxy)-acetanilide. A solution of 45.3 g (0.212 mol) of 4-(2-chloro-ethoxy)-acetanilide in 100 mL of water and 424 mL of 1N HCl was prepared and heated under reflux overnight. The reaction flask was then cooled in an ice bath while aqueous sodium hydroxide was added to the reaction mixture until a pH of 7–8 was obtained. The product which precipitated was removed by filtration, and saved. The filtrate was extracted with ethyl acetate (3×100 mL). The combined organic phases were dried over magnesium sulfate, filtered, evaporated to dryness in a rotary evaporator, and then combined with the first crop of crystals to yield 29.8 g of product. (mp 87–90° C.).

Elemental analysis for $C_8H_{10}ClNO.HCl.0.25\ H_2O$: Calc'd: C, 45.20; H, 5.45; N, 6.59; Found: C, 45.46; H, 5.26; N, 6.44.

EXAMPLE 11

8-Methoxyisatoic Anhydride

To a chilled (0–5° C.) solution of 30.0 g (0.180 mol) of 2-amino-3-methoxybenzoic acid (Aldrich Chemicals) in 500 mL of tetrahydrofuran was added 17.8 g (0.0600 mol) of triphosgene. A precipitate formed upon addition. The ice bath was removed after 15 minutes, and the reaction mixture was stirred for 1 hour at room temperature. The reaction mixture was poured into 1000 mL of water and stirred for thirty minutes. The product (mp 267–268° C.) was filtered and amounted to 32.9 g.

Elemental analysis for $C_9H_7NO_4$: Calc'd: C, 55.96; H, 3.65; N, 7.25; Found: C, 55.77; H, 3.67; N, 7.00.

EXAMPLE 12

2-Amino-N-(4-methoxy-phenyl)-3-methoxy-benzamide

To a solution of 27.17 g (0.141 mol) of 8-methoxyisatoic anhydride in 200 mL of ethanol was added a catalytic amount of 4-dimethylaminopyridine and 350 mL of a 1M solution containing 43.0 g (0.350 mol) of p-anisidine. The reaction mixture was stirred and heated under reflux overnight. The reaction flask was then chilled on ice. The precipitate that formed was collected by vacuum filtration and amounted to 34.7 g. An analytical sample (mp 168–169° C.) was obtained by recrystallization from ethanol.

Elemental analysis for $C_{15}H_{16}N_2O_3$: Calc'd: C, 66.16; H, 5.92; N, 10.29; Found: C, 66.36; H, 5.86; N, 10.30.

EXAMPLE 13

2-[4-(2-Chloro-ethoxy)-phenyl]-8-methoxy-3-(4-methoxy-phenyl)-2,3-dihydro-1H-quinazolin-4-one To a solution of 20.05 g (0.0736 mol) of 2-amino-N-(4-methoxy-phenyl)-3-methoxy-benzamide in 400 mL of ethanol was added 13.6 g (0.0736 mol) of p-(2-chloro-ethoxy)-benzaldehyde (Frinton Labs), and 10 mL of acetic acid. The reaction mixture was stirred and heated to a mild reflux overnight. After cooling to room temperature, the solvent was evaporated in a rotary evaporator. The residue was dissolved in 300 mL of ethyl acetate and washed with water (4×100 mL). The organic phase was removed, dried over magnesium sulfate, filtered and evaporated to dryness in a rotary evaporator. The residual oil was placed under the vacuum pump, which yielded 26.0 g (mp 122–124° C.) of product.

Elemental analysis for $C_{24}H_{23}ClN_2O_4$: Calc'd: C, 65.68; H, 5.28; N, 6.38; Found: C, 65.38; H, 5.27; N, 6.24.

EXAMPLE 14

2-[4-(2-Chloro-ethoxy)-phenyl]-8-methoxy-3-(4-methoxy-phenyl)-3H-quinazolin-4-one To a solution of 18.0 g (0.0410 mol) of 2-[4-(2-chloro-ethoxy)-phenyl]-8-methoxy-3-(4-methoxy-phenyl)-2,3-dihydro-1H-quinazolin-4-one in 500 mL of toluene was added 9.31 g (0.0410 mol) of 2,3-dichloro-5,6-dicyano-1,4-benzoquinone. The reaction mixture was stirred and heated under reflux for 3 hours. After cooling to room temperature, the solvent was removed in a rotary evaporator. Ethanol (300 mL) was added to the crude product and stirred at room temperature overnight. The precipitate was collected by vacuum filtration. An analytical sample (mp 151–152° C.) was obtained by recrystallization from ethanol.

Elemental analysis for $C_{24}H_{21}ClN_2O_4$: Calc'd: C, 65.98; H, 4.85; N, 6.41; Found: C, 65.95; H, 4.71; N, 6.28.

EXAMPLE 15

2-[4-(2-Chloro-ethoxy)-phenyl]-8-hydroxy-3-(4-hydroxy-phenyl)-3H-quinazolin-4-one To a chilled (−30° C.) solution of 6.6 g (0.0151 mol) of 2-[4-(2-chloro-ethoxy)-phenyl]-8-methoxy-3-(4methoxy-phenyl)-3H-quinazolin-4-one in 200 mL of dry methylene chloride was added 50.0 mL (0.0500 mol) of boron tribromide (1M solution in dichloroethane, Aldrich Chemicals). The reaction mixture was stirred under nitrogen at −30° C. for 20 minutes and then at 0–5° C. for 5 hours. The crude reaction mixture was poured into 600 mL of aqueous sodium bicarbonate, and stirred vigorously for 30 minutes. The precipitate which formed was collected by vacuum filtration. An analytical sample (mp 188–190° C.) was obtained by recrystallization from ethanol.

Elemental analysis for $C_{22}H_{17}ClN_2O_4.0.5\ H_2O$: Calc'd: C, 63.24; H, 4.34; N, 6.71; Found: C, 63.25; H, 4.04; N, 6.66.

EXAMPLE 16

8-Hydroxy-3-(4-hydroxy-phenyl)-2-{4-[2-(piperidin-1-yl)-ethoxy]-phenyl}-3H-quinazolin-4-one A solution of 2.82 g (0.00690 mol) of 2-[4-(2-chloro-ethoxy)-phenyl]-8-hydroxy-3-(4-hydroxy-phenyl)-3H-quinazolin-4-one in 20 mL of piperidine was heated to a mild reflux for 3 hours. The piperidine then was evaporated in a rotary evaporator. The crude product was dissolved in 100 mL of ethyl acetate and extracted with 0.1N hydrochloric acid (3×50 mL). The aqueous phase was removed and brought to pH 8–9 with 0.1N potassium hydroxide, and then extracted again with fresh ethyl acetate (3×50 mL). The organic phases were combined, dried over magnesium sulfate, filtered and evaporated to dryness in a rotary evaporator. An analytical sample (mp 153–155° C.) was obtained by recrystallization from ethanol.

Elemental analysis for $C_{27}H_{27}N_3O_4.0.5\ H_2O$: Calc'd: C, 69.51; H, 6.05; N, 9.01; Found: C, 69.57; H, 5.98; N, 8.90.

EXAMPLE 17

2-Amino-N-[4-(2-chloro-ethoxy)-phenyl]-3-methoxy-benzamide

To a solution of 12.9 g (0.0669 mol) of 8-methoxyisatoic anhydride in 500 mL of ethanol was added a catalytic amount of 4-dimethylaminopyridine and 167 mL of a 1M solution containing 28.7 g (0.167 mol) of 4-(2-chloro-ethoxy)-aniline. The reaction mixture was stirred and heated under reflux for 4 hours. After cooling the reaction mixture to room temperature, ½ of the solvent was evaporated in a rotary evaporator. The reaction mixture was cooled on ice. The precipitate that formed was collected by vacuum filtration and amounted to 14.3 g. An analytical sample (mp 197–198° C.) was obtained by recrystallization from ethanol.

Elemental analysis for $C_{16}H_{17}ClN_2O_3.0.25\ H_2O$: Calc'd: C, 59.08; H, 5.42; N, 8.61; Found: C, 59.43; H, 5.19; N, 8.61.

EXAMPLE 18

3-[4-(2-Chloro-ethoxy)-phenyl]-8-methoxy-2-(4-methoxy-phenyl)-2,3-dihydro-1H-quinazolin-4-one To a solution of 13.8 g (0.0430 mol) of 2-amino-N-[4-(2-chloro-ethoxy)-phenyl]-3-methoxy-benzamide in 1200 mL of ethanol was added 5.3 mL (0.0430 mol) of p-anisaldehyde and 25 mL of acetic acid. The reaction mixture was stirred and heated to a mild reflux overnight. The solvent then was evaporated in a rotary evaporator. After the addition of diethyl ether and petroleum ether, the oily residue was chilled on ice. The precipitate that formed was collected by vacuum filtration and amounted to 17.3 g. An analytical sample (mp 144–149° C.) was obtained by recrystallization from ethanol.

Elemental analysis for $C_{24}H_{23}ClN_2O_4.0.25\ H_2O$: Calc'd: C, 65.00; H, 5.34; N, 6.32; Found: C, 65.13; H, 5.26; N, 6.33.

EXAMPLE 19

3-[4-(2-Chloro-ethoxy)-phenyl]-8-methoxy-2-(4-methoxy-phenyl)-3H-quinazolin-4-one To a solution of 17.28 g (0.0394 mol) of 3-[4-(2-chloro-ethoxy)-phenyl]-8-methoxy-2-(4-methoxy-phenyl)-2,3-dihydro-1H-quinazolin-4-one in 300 mL of toluene was added 8.94 g (0.0394 mol) 2,3-dichloro-5,6-dicyano-1,4-benzoquinone. The reaction mixture was stirred and heated to reflux for 3 hours. The toluene then was removed in a rotary evaporator. Methanol (300 mL) was added to the reaction flask which was allowed to stir at room temperature overnight. The precipitate (mp 209–211° C.) was collected by vacuum filtration and amounted to 15.8 g.

Elemental analysis for $C_{24}H_{21}ClN_2O_4$: Calc'd: C, 65.98; H, 4.84; N, 6.41; Found: C, 65.70; H, 4.79; N, 6.33.

EXAMPLE 20

3-[4-(2-Chloro-ethoxy)-phenyl]-8-hydroxy-2-(4-hydroxy-phenyl)-3H-quinazolin-4-one To a chilled (0° C.) solution of 3.5 g (0.00801 mol) of 3-[4-(2-chloro-ethoxy)-phenyl]-8-methoxy-2-(4-methoxyphenyl)-3H-quinazolin-4-one in 100 mL of dry methylene chloride was added 35 mL (0.0352 mol) of boron tribromide (1M solution in dichloroethane (Aldrich Chemicals)). The reaction mixture was stirred at 0° C. for 20 minutes, under nitrogen, and then at room temperature overnight. The crude reaction mixture was added to 400 mL of aqueous sodium bicarbonate. The solution was stirred vigorously for 1 hour at room temperature. The precipitate which formed was collected by vacuum filtration. An analytical sample (mp 274–276° C.) was obtained by recrystallization from methanol.

Elemental analysis for $C_{22}H_{17}ClN_2O_4$: Calc'd: C, 64.63; H, 4.19; N, 6.85; Found: C, 64.24; H, 4.06; N, 6.78.

EXAMPLE 21

8-Hydroxy-2-(4-hydroxy-phenyl)-3-[4-(2-piperidin-1-yl-ethoxy)-phenyl]-3H-quinazolin-4-one A solution containing 2.03 g (0.00497 mol) of 3-[4-(2-chloro-ethoxy)-phenyl]-8-hydroxy-2-(4-hydroxy-phenyl)-3H-quinazolin-4-on in 22 mL of piperidine was stirred and heated to a mild reflux for 2 hours. The piperidine then was evaporated in a rotary evaporator. The crude product was dissolved in 100 mL of ethyl acetate and extracted with 0.1N hydrochloric acid (3–50 mL). The aqueous phase was removed and brought to pH 8–9 with 0.1N potassium hydroxide, and then extracted again with fresh ethyl acetate (3×50 mL). The organic phases were combined, dried over magnesium sulfate, filtered and evaporated to dryness in a rotary evaporator to yield 1.3 g of product. An analytical sample (mp 224–227° C.) was obtained by recrystallization from ethanol.

Elemental analysis for $C_{27}H_{27}N_3O_4 \cdot 0.25\ H_2O$: Calc'd: C, 70.19; H, 6.00; N, 9.10; Found: C, 69.87; H, 6.02; N, 8.87.

PHARMACOLOGY

In vitro estrogen receptor binding assay
Receptor preparation:

Chinese Hamster Ovary (CHO) cells overexpressing the estrogen receptor were grown in 150 mm$^2$ dishes in DMEM+10% dextran coated charcoal, stripped fetal bovine serum. The plates were washed twice with PBS and once with 10 mM Tris-HCl, pH 7.4, 1mM EDTA. Cells were harvested by scraping the surface and then the cell suspension was placed on ice. Cells were disrupted with a hand-held motorized tissue grinder using two 10-second bursts. The crude preparation was centrifuged at 12,000×g for 20 minutes followed by a 60 minute spin at 100,000×g to produce a ribosome free cytosol. The cytosol was then frozen and stored at –80° C. Protein concentration of the cytosol was estimated using the BCA assay with reference standard protein.

Binding assay conditions

The competition assay was performed in a 96-well plate (polystyrene*) which binds <2.0% of the total input [$^3$H]-17-β-estradiol and each data point was gathered in triplicate. 100 μg/100 μL of the receptor preparation was aliquoted per well. A saturating dose of 2.5 nM [$^3$H]17-β-estradiol+ competitor (or buffer) in a 50 μL volume was added in the preliminary competition when 100× and 500× competitor were evaluated, only 0.8 nM [$^3$H] 17-β-estradiol was used. The plate was incubated at room temperature for 2.5 h. At the end of this incubation period 150 μL of ice-cold dextran coated charcoal (5% activated charcoal coated with 0.05% 69K dextran) was added to each well and the plate was immediately centrifuged at 99×g for 5 minutes at 4° C. 200 μL of the supernatant solution was then removed for scintillation counting. Samples were counted to 2% or 10 minutes, whichever occurs first. Because polystyrene absorbs a small amount of [$^3$H]17-β-estradiol, wells containing radioactivity and cytosol, but not processed with charcoal were included to quantitate amounts of available isotope. Also, wells containing radioactivity but no cytosol were processed with charcoal to estimate unremovable DPM of [$^3$H] 17-β-estradiol. Corning #25880-96, 96-well plates were used because they have proven to bind the least amount of estradiol.

Analysis of results

Counts per minute (CPM) of radioactivity were automatically converted to disintegrations per minute (DPM) by the Beckman LS 7500 Scintillation Counter using a set of quenched standards to generate a H# for each sample. To calculate the % of estradiol binding in the presence of 100 or fold 500 fold competitor the following formula was applied:

((DPM sample-DPM not removed by charcoal/(DPM estradiol-DPM not removed by charcoal))×100%=% of estradiol binding For the generation of IC$_{50}$ curves, % binding is plotted vs. compound. IC$_{50}$'s are generated for compounds that show >30% competition at 500× competitor concentration. For a description of these methods, see Hulme, E. C., ed. 1992. Receptor-Ligand Interactions: A Practical Approach. IRL Press, New York.(see especially chapter 8).

TABLE 1

Competition With 17-β-estradiol (0.8 nM) in the Receptor Binding Assay

| Compound | IC$_{50}$ M |
|---|---|
| Tamoxifen | 4.5 × 10$^{-6}$ |
| Raloxifene | 4 × 10$^{-8}$ |
| Example 9 | 6.5 × 10$^{-6}$ |
| Example 16 | Binding not detected at upper limit of assay |
| Example 21 | Binding not detected at upper limit of assay |

Ishikawa Cell Alkaline Phosphatase Assay
Cell Maintenance and Treatment:

Ishikawa cells were maintained in DMEM/F12 (50%:50%) containing phenol red+10% fetal bovine serum and the medium was supplemented with 2 mM Glutamax, 1% Pen/Strap and 1 mM sodium pyruvate. Five days prior to the beginning of each experiment (treatment of cells) the medium was changed to phenol red-free DMEM/F12+10% dextran coated charcoal stripped serum. On the day before treatment, cells were harvested using 0.5% trypsin/EDTA and plated at a density of 5×10$^4$ cells/well in 96-well tissue culture plates. Test compounds were dosed at 10$^{-6}$, 10$^{-7}$ and 10$^{-8}$M in addition to 10$^{-6}$ M (compound)+10$^{-9}$ M 17-β-estradiol to evaluate the ability of the compounds to function as antiestrogens. Cells were treat for 48 h prior to assay. Each 96-well plate contained a 17-β-estradiol control. Sample population for at each dose was n=8.

Alkaline Phosphatase Assay:

At the end of 48 h the media is aspirated and cells are washed three times with phosphate buffered saline (PBS). 50 μL of lysis buffer (0.1 M Tris-HCl, pH 9.8, 0.2% Triton X-100) is added to each well. Plates are placed at –80° C. for a minimum of 15 minutes. Plates are thawed at 37° C. followed by the addition of 150 μL of 0.1 M Tris-HCl, pH 9.8, containing 4 mM para-nitrophenylphosphate (pNPP) to each well (final concentration, 3 mM pNPP).

Absorbance and slope calculations were made using the KineticCalc Application program (Bio-Tek Instruments, Inc., Winooski, Vt.). Results are expressed as the mean±S.D. of the rate of enzyme reaction (slope) averaged over the linear portion of the kinetic reaction curve (optical density readings every 5 minutes for 30 minutes absorbance reading). Results for compounds are summarized as percent of response related to 1 nM 17β-estradiol.

A description of these methods is described by Holinka, C. F., Hata, H., Kuramoto, H. and Gurpide, E. (1986) Effects of steroid hormones and antisteroids on alkaline phosphatase activity in human endometrial cancer cells (Ishikawa Line). Cancer Research, 46: 2771–2774, and by Littlefield, B. A., Gurpide, E., Markiewicz, L., McKinley, B. and Hochberg, R. B. (1990) A simple and sensitive microtiter plate estrogen bioassay based on stimulation alkaline phosphatase in Ishikawa cells; Estrogen action of D5 adrenal steroids. Endocrinology, 6: 2757–2762.

TABLE 2

Ishikawa Alkaline Phosphatase Assay

| Compound | % Activation (Test articles at $10^{-6}$ M concentration) |
|---|---|
| 17-β-estradiol | 100% activity (control) |
| Tamoxifen | 0% activity (45% with 1 nM 17-β-estradiol) |
| Raloxifene | 5% activity (5% with 1 nM 17-β-estradiol) |
| Example 9 | 0% activity (91% with 1 nM 17-β-estradiol) |
| Example 16 | 0% activity (47% with 1 nM 17-β-estradiol) |
| Example 21 | 0% activity (61% with 1 nM 17-β-estradiol) |

2X VIT ERE Transfection Assay

Cell Maintenance and Treatment

Chinese Hamster Ovary cells (CHO) which had been stably transfected with the human estrogen receptor were maintained in DMEM+10% fetal bovine serum (FBS). 48 h prior to treatment the growth medium was replaced with DMEM lacking phenol red+10% dextran coated charcoal stripped FBS (treatment medium). Cells were plated at a density of 5000 cells/well in 96-well plates containing 200 μL of medium/well.

Calcium Phosphate Transfection

Reporter DNA (Fromega plasmid pGL2 containing two tandem copies of the vitellogenin ERE in front of the minimal thymidine kinase promoter driving the luciferase gene) was combined with the β-galactosidase expression plasmid pCH110 (Pharmacia) and carrier DNA (pTZ18U) in the following ratio:

10 μg of reporter DNA
5 μg of pCH110DNA
5 μg of pTZ18U
20 μg of DNA/1 mL of transfection solution The DNA (20 μg) was dissolved in 500 μL of 250 mM sterile $CaCl_2$ and added dropwise to 500 μL of 2X HeBS (0.28 M NaCl, 50 mM HEPES, 1.5 mM $Na_2HPO_4$, pH 7.05) and incubated at room temperature for 20 minutes. 20 μL of this mixture was added to each well of cells and remained on the cells for 16 h. At the end of this incubation the precipitate was removed, the cells were washed with media, fresh treatment media was replaced and the cells were treated with either vehicle, 1 nM 17-β-estradiol, 1 μM compound or 1 μM compound+1 nM 17-β-estradiol (tests for estrogen antagonism). Each treatment condition was performed on 8 wells (n=8) which were incubated for 24 h prior to the luciferase assay.

Luciferase Assay

After 24 h exposure to compounds, the media was removed and each well washed with 2X with 125 μL of PBS lacking $Mg^{++}$ and $Ca^{++}$. After removing the PBS, 25 μL of Promega lysis buffer was added to each well and allowed to stand at room temperature for 15 min, followed by 15 min at −80° C. and 15 min at 37° C. 20 μL of lysate was transferred to an opaque 96 well plate for luciferase activity evaluation and the remaining lysate (5 μL) was used for the β-galactosidase activity evaluation (normalize transfection). The luciferan substrate (Promega) was added in 100 μL aliquots to each well automatically by the luminometer and the light produced (relative light units) was read 10 seconds after addition.

TABLE 3

Infection Luciferase Assay

| Compound | % Activation |
|---|---|
| 17-β-estradiol | 100% activity (control) |
| Tamoxifen | 0% activity (10% with 1 nM 17-β-estradiol) |
| Raloxifene | 0% activity (0% with 1 nM 17-β-estradiol) |
| Example 9 | 72% activity (137% with 1 nM 17-β-estradiol) |
| Example 16 | 14% activity (77% with 1 nM 17-β-estradiol) |
| Example 21 | 6% activity (57% with 1 nM 17-β-estradiol) |

β-Galactosidase Assay

To the remaining 5 μL of lysate 45 μL of PBS was added. Then 50 μL of Promega β-galactosidase 2X assay buffer was added, mixed well and incubated at 37° C. for 1 hour. A plate containing a standard curve (0.1 to 1.5 milliunits in triplicate) was set up for each experimental run. The plates were analyzed on a Molecular Devices specrophotometric plate reader at 410 nm. The optical densities for the unknown were converted to milliunits of activity by mathematical extrapolation from the standard curve.

Analysis of Results

The luciferase data was generated as relative light units (RLUs) accumulated during a 10 second measurement and automatically transferred to a JMP (SAS Inc.) file where background RLUs were subtracted. The β-galactosidase values were automatically imported into the file and these values were divided into the RLUs to normalize the data. The mean and standard deviations were determined from a n=8 for each treatment. Compounds activity was compared to 17-β-estradiol for each plate. Percentage of activity as compared to 17-β-estradiol was calculated using the formula:

$$\% = ((\text{Estradiol-control})/(\text{compound value})) \times 100.$$

These techniques are described by Tzukerman, M. T., Esty, A., Santiso-Mere, D., Danielian, P., Parker, M. G., Stein, R. B., Pike, J. W. and McDonnel, D. P. (1994). Human estrogen receptor transactivational capacity was determined by both cellular and promoter context and mediated by two functionally distinct intramolecular regions (see Molecular Endocrinology, 8: 21–30).

Compounds which have activity greater than thirty percent of the control (1 nM 17-β-estradiol) are considered estrogenic. Those compounds which have greater than forty percent inhibition as compared to control (1 nM 17-β-estradiol) when given in combination with 1 nM 17-β-estradiol are considered to be antiestrogenic.

Pharmaceutical Composition

Compounds of this invention may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutically additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The dosage to be used in the treatment of a specific patient suffering estrogen deficiency must be subjectively determined by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached. Precise will be determined by the administering physician based on experience with the individual subject treated and standard medical principles.

Preferably the pharmaceutical composition is in unit dosage form, e.g., as tablets or capsules. In such form, the composition is sub-divided in unit dose containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

What is claimed is:

1. A compound of the formula:

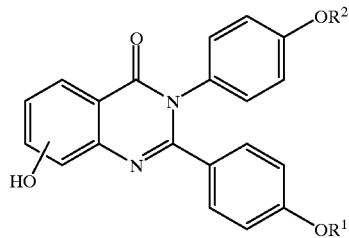

wherein:

R$^1$ and R$^2$ are H or —(CH$_2$)$_n$-pyrrolidinyl, —(CH$_2$)$_n$-piperidinyl, —(CH$_2$)$_n$-homopiperidinyl, or —(CH$_2$)$_n$-morpholinyl; n is 2–3; with a proviso that one, but not both, of R$^1$ and R$^2$ is H;

or a pharmaceutically acceptable salt thereof.

2. A compound according to claim 1 wherein R$^1$ is —(CH$_2$)$_2$-piperidinyl and R$^2$ is H; or a pharmaceutically acceptable salt thereof.

3. A compound according to claim 1 wherein R$^2$ is —(CH$_2$)$_2$-piperidinyl and R$^1$ is H; or a pharmaceutically acceptable salt thereof.

4. A compound according to claim 1 which is 7-hydroxy-2-(4-hydroxy-phenyl)-3-{4-[2-(piperidin-1-yl)-ethoxy]-phenyl}-3H-quinazolin-4-one.

5. A compound according to claim 1 which is 8-hydroxy-3-(4-hydroxy-phenyl)-2-{4-[2-(piperidin-1-yl)-ethoxy]-phenyl}-3H-quinazolin-4-one.

6. A compound according to claim 1 which is 8-hydroxy-2-(4-hydroxy-phenyl)-3-{4-[2-piperidin-1-yl)-ethoxy] phenyl}-3H-quinazolin-4-one.

7. A pharmaceutical composition comprising a pharmaceutically acceptable carrier and a compound of claim 1, or a pharmaceutically acceptable salt thereof.

8. A method of treating osteoporosis, prostatic hypertrophy, breast cancer or endometrial cancer in a mammal, the method comprising administering to a mammal in need thereof a therapeutically effective amount of a compound of claim 1, or a pharmaceutically acceptable salt thereof.

9. The method according to claim 8 wherein the compound used is 7-hydroxy-2-(4-hydroxy-phenyl)-3-{4-[2-(piperidin-1-yl)-ethoxy]-phenyl}-3H-quinazolin-4-one.

10. The method according to claim 8 wherein the compound used is 8-hydroxy-3-(4-hydroxy-phenyl)-2-{4-[2-(piperidin-1-yl)-ethoxy]-phenyl}-3H-quinazolin-4-one.

11. The method according to claim 8 wherein the compound used is 8-hydroxy-2-(4-hydroxy-phenyl)-3-[4-(2-piperidin-1-yl)-ethoxy)-phenyl]-3H-quinazolin-4-one.

* * * * *